( 12 ) United States Patent
Qiao et al.

(10) Patent No.: US 12,350,058 B2
(45) Date of Patent: Jul. 8, 2025

(54) SYSTEM FOR IDENTIFYING PREMATURE VENTRICULAR CONTRACTIONS (71) Applicant: Pacesetter, Inc., Sylmar, CA (US)

(72) Inventors: Yun Qiao, Sunnyvale, CA (US); Fujian Qu, San Jose, CA (US)

(73) Assignee: Pacesetter, Inc., Sylmar (CA)

( * ) Notice: Subject to any disclaimer, the term of this patent is extended or adjusted under 35 U.S.C. 154(b) by 578 days.

(21) Appl. No.: 17/649,039

(22) Filed: Jan. 26, 2022

(65) Prior Publication Data

US 2022/0240830 A1 Aug. 4, 2022

Related U.S. Application Data (60) Provisional application No. 63/145,820, filed on Feb. 4, 2021.

(51) Int. Cl.
A61B 5/346 (2021.01)
A61B 5/349 (2021.01)
A61B 5/352 (2021.01)
A61B 5/363 (2021.01)

(52) U.S. Cl.
CPC .............. A61B 5/349 (2021.01); A61B 5/352 (2021.01); A61B 5/363 (2021.01)

(58) Field of Classification Search
CPC .......... A61B 5/349; A61B 5/363; A61B 5/352
See application file for complete search history.

(56) References Cited

U.S. PATENT DOCUMENTS 4,181,135 A 1/1980 Andresen et al.
8,437,851 B2 5/2013 Corbucci et al.
8,457,728 B2 6/2013 Schneider et al.
9,675,270 B2 6/2017 Sarkar
2004/0158295 A1 8/2004 Dyjach et al.
2005/0234353 A1 10/2005 Xue et al.
2011/0184297 A1 7/2011 Vitali et al.

(Continued)

FOREIGN PATENT DOCUMENTS

CN 102274029 A 12/2011
CN 107397547 A 11/2017
CN 107456227 A 12/2017

OTHER PUBLICATIONS

Extended European Search Report for corresponding EP Application No. 22150268.5-1113 dated Sep. 6, 2022 (9 pages).

(Continued)

Primary Examiner — Eric D. Bertram
(74) Attorney, Agent, or Firm — Dean D. Small; The Small Patent Law Group, LLC (57) ABSTRACT A system is provided that includes one or more processors, and a memory coupled to the one or more processors. The memory stores program instructions, and the program instructions are executable by the one or more processors. When executed, the one or more processors obtain cardiac activity (CA) signals for a series of beats, and identify whether a characteristic of interest (COI) from a first segment of the CA signals exceeds a COI limit. The one or more processors also analyze morphology of the CA signals for the series of beats responsive to the first segment of the CA signals exceeding the COI limit, and based on the analyze operation, identify a premature ventricular contraction (PVC) within the series of beats.

18 Claims, 6 Drawing Sheets (56) References Cited

U.S. PATENT DOCUMENTS

2016/0310031 A1* 10/2016 Sarkar ................... A61B 5/686
2019/0336031 A1* 11/2019 Malhotra ............. A61B 5/0245
2019/0336083 A1* 11/2019 Gill ....................... A61B 5/686
2020/0383597 A1* 12/2020 Rajagopal ............. A61B 5/352

OTHER PUBLICATIONS

Ittatirut et al. "Detection of Premature Ventricular Contraction for Real-Time Applications" IEEE; 2013 (5 pages).
First Office Action mailed Jul. 15, 2024 for corresponding Application No. 202210099828.1 (11 pages).
English translation of the First Office Action mailed Jul. 15, 2024 for corresponding Application No. 202210099828.1 (13 pages).
Second Office Action mailed Nov. 18, 2024 for corresponding Application No. 202210099828.1 (8 pages).
English translation of the Second Office Action mailed Nov. 18, 2024 for corresponding Application No. 202210099828.1 (12 pages).
Second Office Action mailed Dec. 10, 2024 for corresponding Application No. 22 150 268.5 (4 pages).
Rejection Decision for corresponding CN Application No. 202210099828.1 mailed Feb. 25, 2025. English translation provided. (20 pages).

* cited by examiner

SYSTEM FOR IDENTIFYING PREMATURE VENTRICULAR CONTRACTIONS

RELATED APPLICATION

This application relates to and claims priority benefits from U.S. Provisional Application No. 63/145,820, entitled "SYSTEM FOR IDENTIFYING A PREMATURE VENTRICULAR CONTRACTION," filed Feb. 4, 2021, which is hereby incorporated by reference in its entirety.

BACKGROUND

Embodiments herein generally relate to a system for identifying premature ventricular contractions (PVCs), and methods and systems for reducing false cardiac rhythm declarations resulting from the PVCs.

Implantable cardiac monitors (ICMs) operate to monitor the heart, including detecting arrhythmias based on various criteria. Such irregularities can include variation patterns in the cardiac activity (CA) signals. In some embodiments, the arrhythmia detection process steps beat by beat through the CA signals and analyzes the characteristics of interest (COI) over a period of time. An arrhythmia episode can be declared based on the COI. When the ICM detects an arrhythmia episode, the ICM stores the CA signals (e.g. electrocardiograms or EGM signals).

However, arrhythmia detection processes at times may declare false arrhythmia episodes when a patient is not experiencing an arrhythmia. When a false arrhythmia episode is declared, the ICM continues to store the CA signals associated with the episode. False arrhythmia detection may arise due to various conditions and behavior of the heart, such as when a patient experiences sick sinus syndrome with irregular R-wave to R-wave (RR) intervals, experiences frequent PVCs and/or inappropriate R-wave sensing. PVCs, in general, introduce unstable RR intervals, such as short-long RR intervals, where the instability may give rise to erroneous declaration of an AF episode. Thus, PVCs present a substantial challenge in connection with atrial fibrillation (AF) detection algorithms that rely on RR interval variability.

PVCs themselves are generally considered to be benign in the absence of structural heart disease. However, in patients with structural heart disease, presence of PVCs is associated with poorer outcomes when compared to patients without PVCs. Frequent PVCs have also been shown to contribute to cardiomyopathy and heart failure. In patients with PVC-induced cardio myopathy, suppressing PVCs could lead to improved cardiac function by minimizing left ventricle (LV) dysfunction induced by the frequent PVCs.

Achieving reliable detection of PVCs with an ICM poses challenges when compared with PMs and implantable cardiac devices (ICDs) with dedicated atrial and ventricular leads or Holter monitors with multiple surface ECG leads. In addition, it is also challenging to distinguish between PVCs and conducted premature atrial contractions (PACs) while recognizing PVCs with different morphologies originating from various parts of the ventricles.

SUMMARY

In accordance with embodiments herein, a system is provided that includes one or more processors, and a memory coupled to the one or more processors. The memory stores program instructions, and the program instructions are executable by the one or more processors. When executed, the one or more processors obtain cardiac activity (CA) signals for a series of beats, and identify whether a characteristic of interest (COI) from a first segment of the CA signals exceeds a COI limit. The one or more processors also analyze morphology of the CA signals for the series of beats responsive to the first segment of the CA signals exceeding the COI limit, and based on the analyze operation, identify a premature ventricular contraction (PVC) within the series of beats.

Optionally, the one or more processors also, in order to identify whether the COI from the first segment of the CA signals exceeds the COI limit compare a R-R interval (RRI) of a candidate beat to a RRI related to the series of beats, and determine whether a change in the RRI of the candidate beat compared to the RRI related to the series of beats exceeds a threshold. In one aspect, to identify whether the COI from the first segment of the CA signal exceeds the COI limit also includes discarding either the candidate beat, or another beat of the series of beats based on the analyze operation. In another aspect, to analyze morphology of the CA signals for the series of beats includes determining at least one of an area of the CA signals, a maximum amplitude of the CA signals, or a minimum amplitude of the CA signals.

Optionally, the program instructions are executable by the one or more processors to also repeat the obtain, identify, analyze, operations to identify an additional PVC in the series of beats, and determine a type of PVC based on the PVC and the additional PVC. In one aspect, the program instructions are executable by the one or more processors to also reject an AF diagnosis based on identification of the PVC. In another aspect, the program instructions are executable by the one or more processors to also diagnose a type of tachycardia episode based on the identification of the PVCs. In one example, the program instructions are executable by the one or more processors to also discard the RRI of a candidate beat from a heart rate variability (HRV) diagnosis determination responsive to identifying the PVC of the candidate beat. In another example, the program instructions are executable by the one or more processors to also analyze RR's of additional candidate beats responsive to identifying the PVC of the candidate beat, and determine whether a biphasic reaction occurred in the series of beats.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

All references, including publications, patent applications and patents, cited herein are hereby incorporated by reference to the same extent as if each reference were individually and specifically indicated to be incorporated by reference and were set forth in its entirety herein.

Terms

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes and/or by electrodes positioned within or proximate to the heart wall and/or chambers of the heart.

The terms "beat" and "cardiac event" are used interchangeably and refer to both normal and/or abnormal events.

The term "morphology", as used herein, refers to COI of a CA signal. Such characteristics of interests can be of a segment of a CA signal, and can include waveform, wavelength, an interval or segment of the CA signal, amplitude, frequency, minimum amplitude, maximum amplitude, area under a wave form, wavelength, etc.

The term "obtains" and "obtaining", as used in connection with data, signals, information, and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

Embodiments may be implemented in connection with one or more implantable medical devices (IMDs). Non-limiting examples of IMDs include one or more of neurostimulator devices, implantable cardiac monitoring and/or therapy devices. For example, the IMD may represent a cardiac monitoring device, pacemaker, cardioverter, cardiac rhythm management device, implantable cardioverter defibrillator (ICD), neurostimulator, leadless monitoring device, leadless pacemaker, an external shocking device (e.g., an external wearable defibrillator), and the like. For example, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Additionally or alternatively, the IMD may include one or more structural and/or functional aspects of the device(s) described in U.S. Pat. No. 9,333,351 "Neurostimulation Method and System to Treat Apnea" and U.S. Pat. No. 9,044,710 "System and Methods for Providing A Distributed Virtual Stimulation Cathode for Use with an Implantable Neurostimulation System", which are hereby incorporated by reference. Further, one or more combinations of IMDs may be utilized from the above incorporated patents and applications in accordance with embodiments herein.

Additionally or alternatively, the IMD may include one or more structural and/or functional aspects of the device(s) described in U.S. Pat. No. 9,216,285 "Leadless Implantable Medical Device Having Removable and Fixed Components" and U.S. Pat. No. 8,831,747 "Leadless Neurostimulation Device and Method Including the Same", which are hereby incorporated by reference. Additionally or alternatively, the IMD may include one or more structural and/or functional aspects of the device(s) described in U.S. Pat. No. 8,391,980 "Method and System for Identifying a Potential Lead Failure in an Implantable Medical Device", U.S. Pat. No. 9,232,485 "System and Method for Selectively Communicating with an Implantable Medical Device", EP Application No. 0070404 "Defibrillator" and, U.S. Pat. No. 5,334,045 "Universal Cable Connector for Temporarily Connecting Implantable Leads and Implantable Medical Devices with a Non-Implantable System Analyzer", U.S. patent application Ser. No. 15/973,126, titled "Method And System For Second Pass Confirmation Of Detected Cardiac Arrhythmic Patterns"; U.S. patent application Ser. No. 15/973,351, Titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns" which are hereby incorporated by reference.

Additionally or alternatively, the IMD may be a leadless cardiac monitor (ICM) that includes one or more structural and/or functional aspects of the device(s) described in U.S. patent application Ser. No. 15/084,373, filed Mar. 29, 2016, entitled, "Method and System to Discriminate Rhythm Patterns in Cardiac Activity"; U.S. patent application Ser. No. 15/973,126, titled "Method And System For Second Pass Confirmation Of Detected Cardiac Arrhythmic Patterns"; U.S. patent application Ser. No. 15/973,351, titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns", which are expressly incorporated herein by reference.

Provided is an ICM that includes a device algorithm for detecting PVCs. The ICM monitors a Cal of a segment of a CA signal, and in one embodiment the median R-R interval (RRI) for a series of beats of the heart, and upon a new beat of the series of beats being below a threshold, monitoring for the PVC is triggered. In particular, at that time, the morphology of the CA signals for the series of beats are analyzed to determine if a PVC is provided. From the morphology, if a PVC is identified, the type of PVC similarly is identified to calculate the PVC burden of a patient over various time periods. By identifying the PVCs, including the type of PVCs, false diagnosis, such as AF diagnosis can be prevented, or remedial measures may be taken to reduce the effect of the PVC on the patient.

In particular, the device algorithm identifies single PVCs, bigeminy, trigeminy, doublet and triplet PVCs from intrinsic beats, and conducted premature atrial contractions (PACs). Specifically, the PVC has a shorter cycle length, or coupling interval, compared to the intrinsic rhythm. Additionally, the PVC has a non-intrinsic morphology, because the abnormal impulse originated in the ventricles is not propagated through the normal conduction system. As such, the device algorithm is performed on a beat-by-beat basis and compares each RRI and morphology to a rolling buffer of normal intrinsic beat. To reduce the calculation burden of the device algorithm, the morphology comparison is only performed when a ventricular sensed (VS) event is identified as premature based on the RRI. A PVC can be identified by the algorithm if the RRI is significantly shorter and the morphology is significantly different from the intrinsic beats in the rolling buffer.

The device algorithm also accounts for normal fluctuations in heart rate due to activity and circadian rhythm by maintaining an RRI rolling buffer and a morphology rolling buffer consisting of intrinsic beat that are updated in a first-in first-out manner with every beat. The RRI rolling buffer can include three intrinsic RRI values. In other words, the pre and post-PVC intervals are excluded from the RRI rolling buffer. The morphology rolling buffer includes electrograms (EGMs) associated with the last three intrinsic beat. In one example, the EGM of each beat is obtained from 20 ms before the VS marker to 180 ms after the VS marker for a toral duration of 200 ms. The intrinsic EGMs stored in the morphology rolling buffer function as templates for comparison with premature beats.

Figure 1:
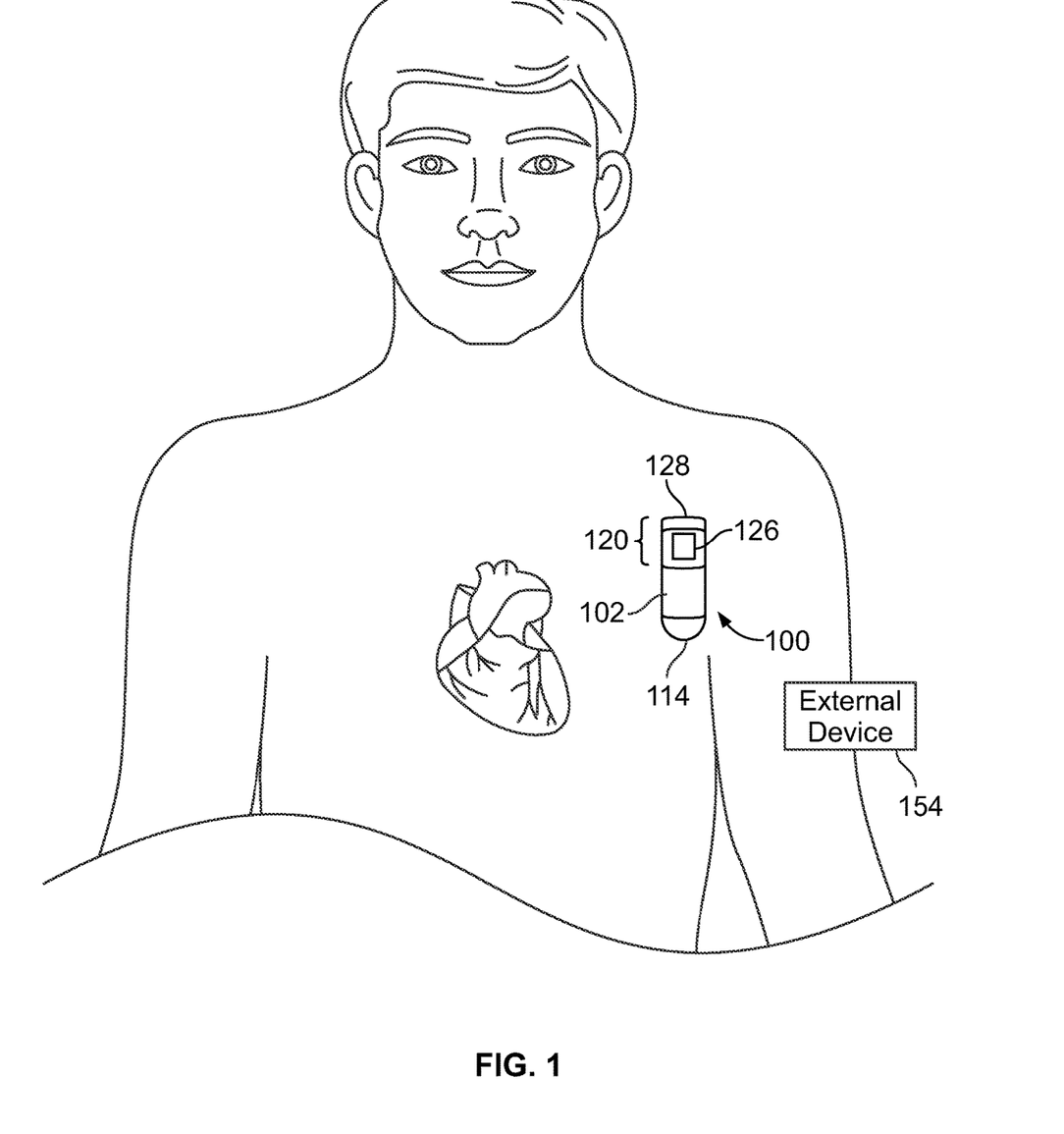
FIG. 1 illustrates a schematic diagram of an ICM in accordance with embodiments herein.

FIG. 1 illustrates an ICM 100 intended for subcutaneous implantation at a site near the heart. While an ICM is provided, in an alternative embodiment the system can be an ICD, including a subcutaneous ICD. The ICM 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The ICM 100 may be configured to be activated by the patient or automatically activated, in connection with recording subcutaneous ECG signals.

The ICM 100 senses far field, subcutaneous CA signals, processes the CA signals to detect arrhythmias and if an arrhythmia is detected, automatically records the CA signals in memory for subsequent transmission to an external device. The CA signal processing and AF detection is provided for, at least in part, by algorithms embodied in or implemented by the microprocessor. The ICM 100 includes one or more processors and memory that stores program instructions directing the processors to implement AF detection utilizing an on-board RRI irregularity (ORI) process that analyzes cardiac activity signals collected over one or more sensing channels. To this end, the ICM can obtain a COI of a segment of a CA signal such as an RRI. The COI is then compared to a COI limit to determine if a threshold has been exceeded. Specifically, in one example, based on the RRI obtained, the ICM determines if the RRI is below a threshold to trigger analyzing the morphology of a series of beats to identify a PVC.

In one example, the RRI is below a determined threshold that may be a specific period of time. Alternatively, an RRI median value for a determined number of beats for a series beats are continuously calculated by one or more processors of a controller. If the RRI falls below a percentage threshold below the median, the one or more processors of the controller then analyze the morphology of the CA signal. In such an example, only a determined number of beats are utilized to determine the RRI median in a first in first out manner. As a result, only the most recent RRIs are utilized in making the RRI median calculation. By using only the most recent RRIs, the one or more processors account for variation of the RRI due to exercise, posture change, sleep, excitement, etc. not related to a PVC. In this manner, unnecessary monitoring, and waste of energy is avoided.

Figure 2:
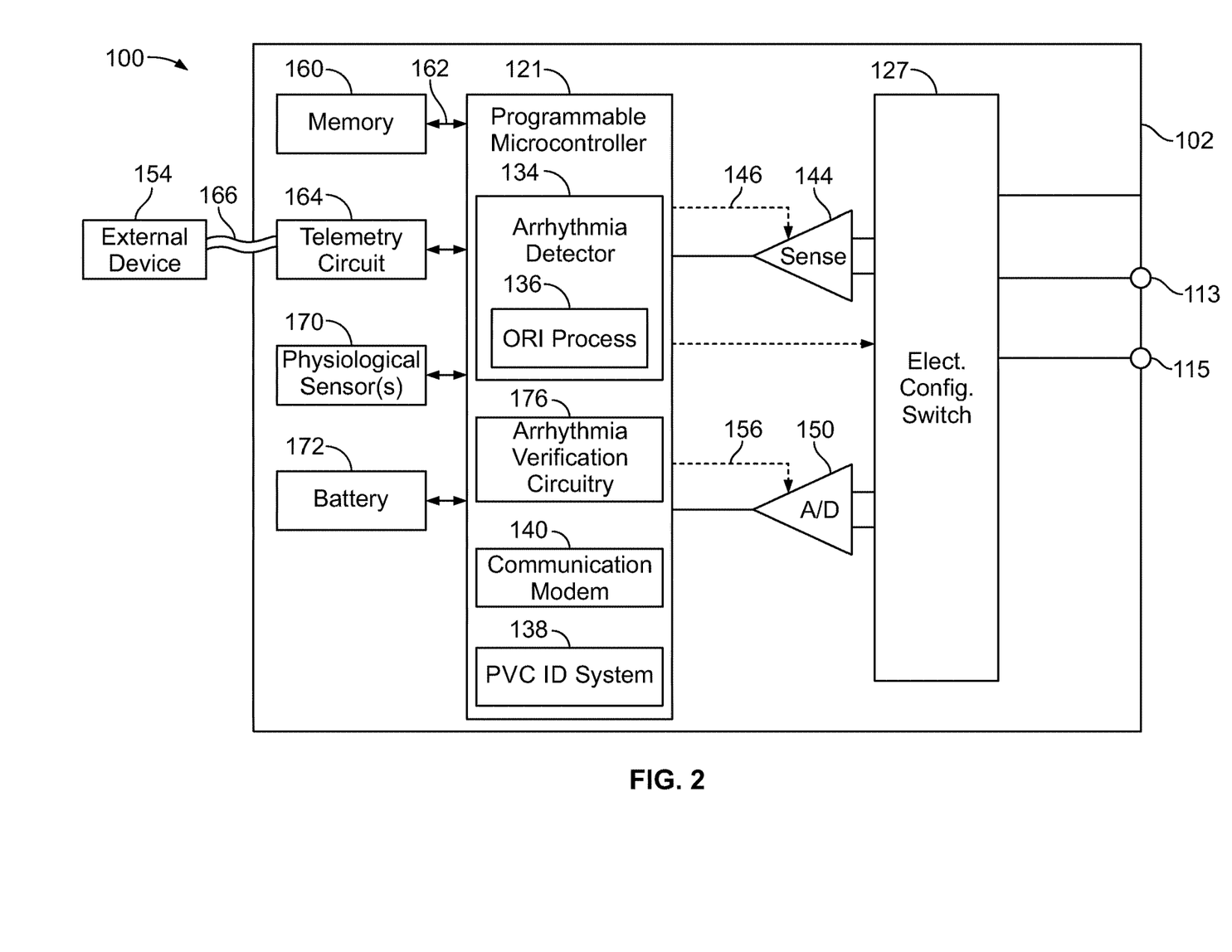
FIG. 2 illustrates a schematic block diagram of an ICM in accordance with embodiments herein.

FIG. 2 shows a block diagram of the ICM 100 formed in accordance with embodiments herein. The ICM 100 may be implemented to monitor ventricular activity alone, or both ventricular and atrial activity through a sensing circuit. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/ or ROM memory, logic and timing circuitry, state machine circuitry, and I/O circuitry. The microcontroller 121 also performs the operations described herein in connection with obtaining CA signals and analyzing the CA signals.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal from the microcontroller 121. Optionally, the switch 127 may be omitted and the I/O circuits directly connected to the housing electrode 114 and a second electrode 126.

Microcontroller 121 includes an arrhythmia detector 134 that is configured to analyze cardiac activity signals to identify potential arrhythmia episodes (e.g., Tachycardias, Bradycardias, Asystole, Brady pause, atrial fibrillation, etc.). By way of example, the arrhythmia detector 134 may implement an arrhythmia detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies. The arrhythmia detector 134 of the microcontroller 121 includes an ORI process 136 that detects arrhythmia episodes, such as AF episodes using R-R interval irregularities, and monitors for triggering analysis to identify PVCs. The ORI process 136 may be implemented as firmware, software and/or circuits. The ORI process 136 uses a hidden Markov Chains and Euclidian distance calculations of similarity to assess the transitionary behavior of one RRI to another and compare the patient's RRI transitions to the known RRI transitions during atrial fibrillation (AF) and non-AF episodes obtained from the same patient and/or many patients.

The arrhythmia detector 134 analyzes sensed far field CA signals sensed along a sensing vector between a combination of subcutaneous electrodes for one or more beats. The arrhythmia detector 134 identifies one or more features of interest from the CA signals, and based on further analysis of the features of interest determines whether the CA signals are indicative of a normal sinus rhythm or an arrhythmia episode.

The ICM also includes a PVC identification system 138 that is coupled to the arrhythmia detector 134. In particular, the PVC identification system 138 monitors a COI of a segment of a CA signal to determine whether or not to trigger determining if a CA signal provides a PVC. In one example, the COI is an RRI, and the RRI of each CA signal is analyzed to determine if any given RRI falls below a threshold that may be as a result of a PVC. In one example, a median RRI of CA signals for a series of beats is continuously calculated. Specifically, in one example, the median is calculated only for the most recent three beats. In this manner, when events occur such as exercise, sleep, posture change, or the like, that naturally varies the RRI, such variance is considered.

When a RRI is below the threshold, the PVC identification system 138 then determines the morphology of the CA signal. The morphology of the CA signal is analyzed to identify if a PVC has occurred, and the type of PVC that has occurred. In one example, the morphology of the CA signal is compared to the morphologies of CA signals that represent a determined PVC. In example embodiments, the comparison can be of only a segment of the morphology, including an area of a CA signal, amplitude, frequency, or the like. Such determination may be made utilizing a lookup table, mathematical model, mathematical function, calculation, or the like.

The ICM 100 is further equipped with a communication modem (modulator/demodulator) 140 to enable wireless communication. In one implementation, the communication modem 140 uses high frequency modulation, for example using RF, Bluetooth, or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuit 144 selectively coupled to one or more electrodes that perform sensing operations, through the switch 127 to detect cardiac activity data indicative of cardiac activity. The sensing circuit 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuit 144 is connected to the microcontroller 121 which, in turn, determines when to store the cardiac activity data of CA signals (digitized by the A/D data acquisition system 150) in the memory 160. For example, the microcontroller 121 may only store the cardiac activity data (from the A/D data acquisition system 150) in the memory 160 when a potential arrhythmia episode is detected. The sensing circuit 144 receives a control signal 146 from the microcontroller 121 for purposes of controlling the gain, threshold, polarization charge removal circuitry (not shown), and the timing of any blocking circuitry (not shown) coupled to the inputs of the sensing circuit.

Optionally, the ICM 100 may include multiple sensing circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or in a bipolar sensing configuration. Optionally, the sensing circuit 144 may be removed entirely and the microcontroller 121 perform the operations described herein based upon the CA signals from the A/D data acquisition system 150 directly coupled to the electrodes.

The ICM 100 further includes an analog-to-digital A/D data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential arrhythmia episodes. The ACS adjustment and ORI process 136 may be applied to signals from the sensing circuit 144 and/or the DAS 150.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smartwatch, and the like) that can be coupled over a network (e.g., the Internet) to a remote monitoring service, medical network, and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, AF detection criteria, activity sensing or other physiological sensors, and electrode polarity, PVC identification, etc.

In addition, the memory 160 stores the CA signals, and other data content associated with detection of arrhythmia episodes, PVCs, or the like. The operating parameters of the ICM 100 may be non-invasively programmed into the memory 160 through a telemetry circuit 164 in telemetric communication via communication link 166 with the external device 154. The telemetry circuit 164 allows intracardiac electrograms and status information relating to the operation of the ICM 100 (as contained in the microcontroller 121 or memory 160) to be sent to the external device 154 through the established communication link 166. In accordance with embodiments herein, the telemetry circuit 164 conveys the DCA data sets and other information related to arrhythmia episodes to an external device.

The ICM 100 can further include one or more physiologic sensors 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable. See for example, U.S. Pat. No. 7,294,108, Cardiac event micro-recorder and method for implanting same, which is hereby incorporated by reference.

The ICM also optionally includes arrhythmia verification circuitry 176 that is configured to implement one or more of the operations discussed herein. The arrhythmia verification circuitry 176 is configured to be a computer implemented method for reducing false declarations of arrythmias based on oversensing or undersensing of R-waves of the CA signals. The arrhythmia verification circuitry 176 obtains CA signals, at the electrodes of the IMD 100, in connection with multiple cardiac beats and, in connection with the CA signals, obtains motion data indicative of one or more of a patient posture or a respiration cycle. The method obtains motion data at one or more physiological sensors 170 (e.g., an accelerometer) and/or via a cardiac impedance (CI) sensing circuit of the IMD 100 generated during the cardiac beats. Such obtained motion data may be utilized to determine if motion has resulted in a false AF diagnosis. In addition, the arrhythmia verification circuitry 176 is coupled to and communicates with the PVC identification system 138 to determine if a PVC similarly has resulted in a false AF diagnosis.

The arrhythmia verification circuitry 176 identifies whether a Cal from a first segment of the CA signals exceeds a COI limit and analyzes motion data to determine whether the at least one of the posture or the respiration cycle at least in part caused the COI to exceed the COI limit. Posture includes postural states and/or activity levels of a patient including supine, laying on a right side, laying on a left side, sitting, standing, isometric arm exercises (e.g., pushing, pulling, and the like), ballottement, chest thump, device pressure (e.g., top, mid, and base), arm flap, handshake, and the like. Activity level in example embodiments include types of activity currently experienced by a patient, including stationary state, rest state, exercise state, walking state, and the like. In addition, the PVC identification system 138 analyzes the CA signals to determine if a PVC has occurred. In this manner, the arrhythmia verification circuitry 176 also analyzes the PVC identification to determine if the PVC caused the AF diagnosis.

Figure 3:
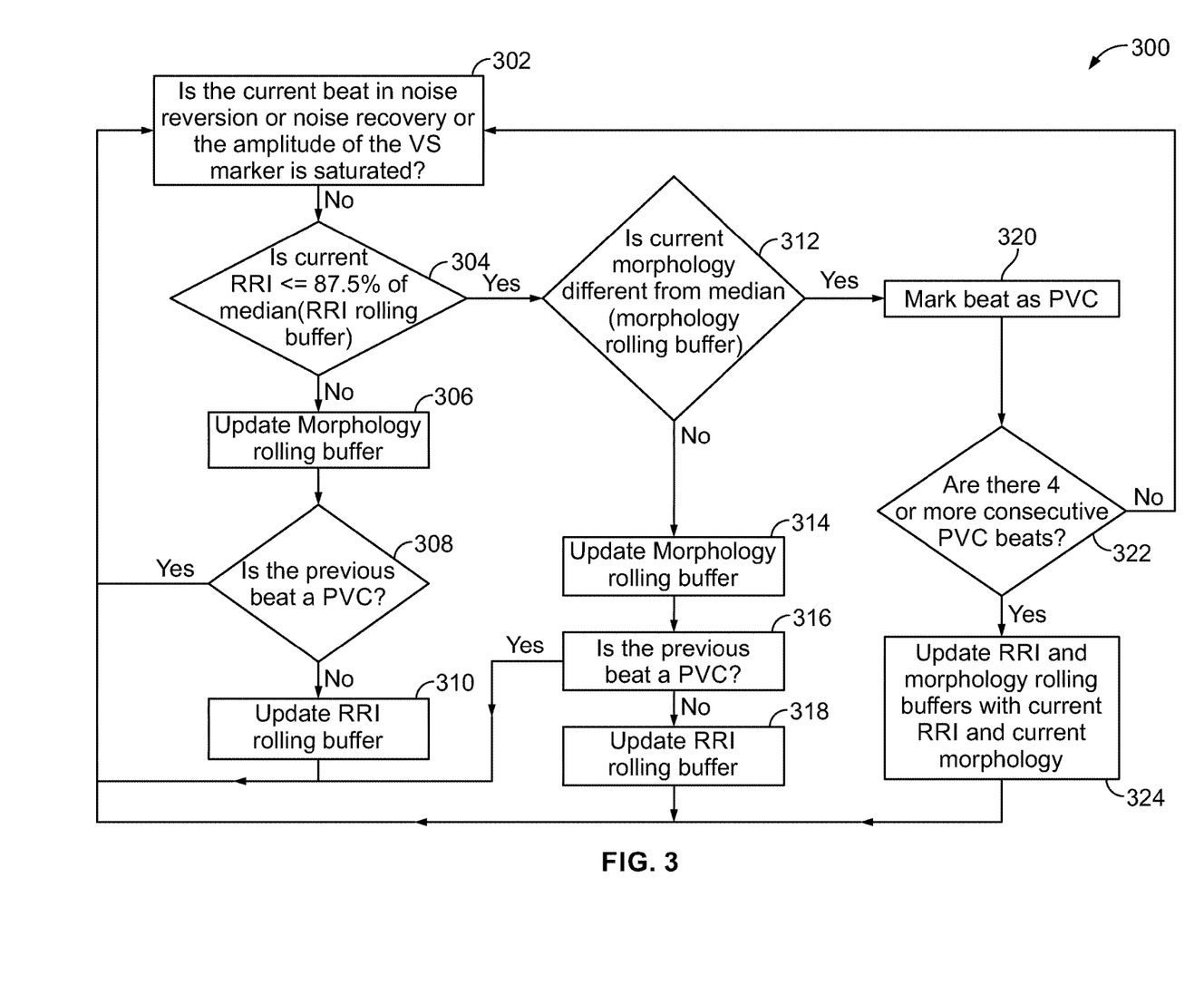
FIG. 3 illustrates a block flow diagram of a method for identifying PVCs in accordance with embodiments herein.

FIG. 3 illustrates a method 300 for identifying PVCs. In one example, one or more processors of a ICM implement the method 300. In an alternative embodiment the system performing the method can be an ICD, including a subcutaneous ICD. In another example, the method is implemented by the ICM described in FIGS. 1-2. The method 300 is provided by an ICM that continuously monitors a series of beats of a patient's heart. In another example, all median operators used in method 300 can be replaced with mean operator.

Figure 4:
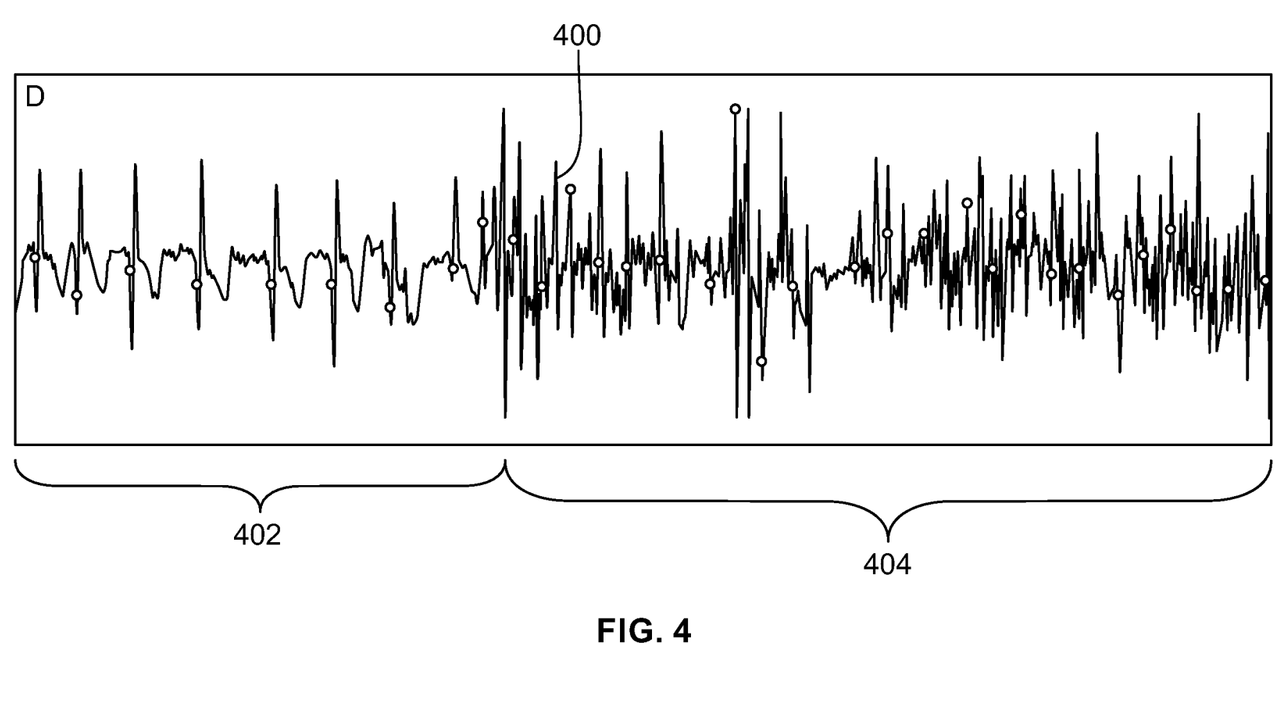
FIG. 4 illustrates of graph of a CA signal in accordance with embodiments herein.

At 302, for a candidate beat, the one or more processors determine if a noise threshold is exceeded for the beat. Specifically, to prevent inappropriate detection due to noise oversensing, the algorithm is paused when the device is in noise reversion or noise recovery, or when the wideband EGM amplitude at the VS marker is saturated. In one example, the noise is detected when multiple noise threshold crossings have occurred in a short detection window. The noise sensing threshold can range from 3-127 analog-to-digital converter (ADC) counts. The number of noise threshold crossings can range from 2 to 8. The noise detection window can range from 50-60 ms. In this manner, if too much noise for a CA signal of a candidate beat is determined, the signal is discarded, and no determination is made regarding whether a PVC is presented. FIG. 4 illustrates an example CA signal 400 that includes a first section 402 where a noise threshold is not exceeded, and a second section 404 where the noise threshold is exceeded. As illustrated, the excess noise of the second section could result in faulty readings and diagnosis, such that the one or more processors do not identify PVCs for such a segment of a CA signal.

If at 302 the noise threshold is not exceeded, then at 304, the one or more processors determine if a COI of a segment of a CA signal exceeds a COI limit. In one example the COI is a RRI of a candidate beat, and if the RRI is below a threshold related to the series of beats, the COI limit is exceeded. The threshold is related to the series of beats because the series of beats may be analyzed as a whole. For example, the threshold may be based on an average of the series of beats, a portion of the series of beats, etc. In another example, the threshold related to the series of beats is a specific period of time determined based on the series of beats. Alternatively, an RRI median value for the series of beats, a portion of the series of beats, etc. are continuously calculated. If the RRI falls below a percentage threshold below the median, the one or more processors analyze the morphology of the CA signal. In such an example, only a determined number of beats are utilized to determine the RRI median in a first in first out manner. As a result, only the most recent RRIs are utilized in making the RRI median calculation. Specifically, the one or more processors account for varying RRI due to exercise, sleeping, posture changes, etc.

In one example, the threshold for a candidate CA signal is less than 87.5% of a median of the previous three CA signals. By continuously monitoring and determining if the RRI of a most recent, candidate CA signal is below the threshold, and not moving forward with analyzing whether the CA signals present a PVC until such a threshold is exceeded, the threshold presents a buffer for preventing battery use to identify if a PVC is present when a PVC is not presented. After analyzing the candidate CA signal, the candidate CA signal either is discarded as a PVC, or becomes part of the series of beats from which additional candidate beats are compared. When the candidate beat is added to the series of beat from which additional candidate beats are compared, the oldest beat of the series of beats is discarded. Because of the first in first out process, wherein only the most recent beats are analyzed, and CA signals are considered in determining if the threshold is exceeded, the process is considered a rolling buffer in that the threshold is continuously updated and varied.

If at 304 the candidate beat does not exceed the COI limit, then at 306, the one or more processors update a CA signal morphology. Specifically, just as the most recent CA signals can be utilized to determine a median threshold based on RRI, the CA signals can also be utilized to determine an averaged, or median morphology of the CA signals. This CA signal morphology can then be compared to the morphology of future CA signals to determine if a PVC is presented. Again, by utilizing the most recent CA signal morphology, factors such as posture, movement, exercise, etc. that may naturally affect the CA signal morphology is considered to prevent a false detection of a PVC. In this manner, the COIs obtained may be compared and analyzed against the most relevant CA signals.

At 308, after updating the CA signal morphology, a determination is made whether a previous beat had been a PVC. If the previous beat had been a PVC, then the one or more processor goes back to monitoring the CA signals. In an example embodiment when the COI is the RRI, if the previous beat was not a PVC, then at 310, the one or more processors update the RRI threshold. Specifically, the oldest CA signal recorded in the memory is discarded, and the CA signal RRI is included in the determination of the threshold for analyzing the next CA signal. In this manner, a RRI rolling buffer, similar to the morphology rolling buffer is provided. After updating the RRI threshold, again, the one or more processors continue monitoring CA signals.

In particular, the method 300 accounts for normal fluctuations in heart rate due to activity and circadian rhythm by maintaining an RRI rolling buffer and the morphology rolling buffer that consists of intrinsic beats, which are updated in a first-in first-out fashion with every beat if the current beat is not determined to be a PVC. In one embodiment, the RRI rolling buffer includes three intrinsic RRI values. In other words, the pre and post-PVC intervals are excluded from the RRI rolling buffer. Meanwhile, in the embodiment, the morphology rolling buffer includes EGMs associated with the last three intrinsic beats. The EGM of each beat can be taken from 20 ms before the VS marker to 180 ms after the VS marker for a total duration of 200 ms. The intrinsic EGMs stored in the morphology rolling buffer in order to function as templates for comparison with premature beats.

To this end, if at 304, the COI limit is exceeded, then the one or more processors at 312 analyze morphology of the CA signals for the series of beats responsive to the first segment of the CA signals exceeding the COI limit. In one example, the one or more processors determine a median morphology based on the three most recent non-PVC CA signals analyzed. By utilizing the most recent CA signals, again, changes including for physical activity, sleeping, etc. are prevented from resulting in an incorrect diagnosis of a PVC. In one embodiment, analysis is provided by comparing the morphology to the median morphology. By comparing the morphology of a current CA signal to previous morphologies of CA signals of the patient, a patient specific analysis is undertaken, improving accuracy.

In one example, the morphology is compared by comparing the area of the CA signal to the morphology of a median CA signal. Such a comparison is made as follows:

$$\text{Area: if sum(abs(EGM))} >= \text{threshold1} * \text{median}$$

Where abs (EGM) is the absolute value of the area CA signal, threshold1 is a constant determined threshold value that in example embodiments is 1.8125, and median is the area in morphology of the median rolling buffer.

In another example, the morphology comparison is based on a maximum, or positive amplitude of the CA signal. In such an embodiment the comparison is determined as follows:

$$\text{Positive amplitude: if abs(max(EGM)} - \text{median(Max Amp}_{median}\text{))} >= \text{threshold2} * \text{abs(median(Max Amp}_{median}\text{))} > 0.15 \text{ mV}$$

Where max(EGM) is the maximum positive amplitude, median(Max Amp$_{median}$) is the maximum amplitude of the median morphology, threshold2 is a constant determined threshold value that in example embodiments is 0.8125, and abs(median(Max Amp$_{median}$) is an absolute value of the maximum amplitude of the median morphology.

In another example, the morphology comparison is based on a minimum, or maximum negative amplitude of the CA signal. In such an embodiment the comparison is determined as follows:

$$\text{Negative amplitude: if abs(min(EGM)} - \text{median(Min Amp}_{median}\text{))} >= \text{threshold2} * \text{abs(median(Min Amp}_{median}\text{))} \text{ AND abs(min(EGM)} - \text{median(Min Amp}_{median}\text{))} > 0.15 \text{ mV}$$

Where min(EGM) is the negative amplitude, and median (Min Amp$_{median}$) is the minimum amplitude of the median morphology, threshold2 is a constant determined threshold value that in example embodiments is 0.8125, and abs (median(Max Amp$_{median}$) is an absolute value of the maximum amplitude of the median morphology In another example, the morphology comparison is based on the polarity of the CA signal. In such an embodiment the comparison is determined as follows:

$$\text{Polarity Change: xor(medianPolarity} >= 0, \text{max (EGM)} + \text{min(EGM)} >= 0) \text{ AND abs(medianPolarity} - (\text{max(EGM)} + \text{min(EGM)})) > 0.2 \text{ mV};$$
$$\text{medianPolarity} = \text{mean(Max Amp}_{median}) + \text{mean (Min AMP}_{median})$$

Where max(EGM) is the value of the maximum amplitude, and min(EGM) is the value of the minimum amplitude.

In one example, when compared with the beats in the morphology rolling buffer, if the premature beat meets any of the four conditions, the beat is identified as a PVC. Otherwise, the beat is considered as intrinsic and the rolling buffers are updated accordingly.

If at 312, the CA signal for the series of beats is determined to not be a PVC, then at 314, the one or more processors update a CA signal morphology. Specifically, just as the most recent CA signals can be utilized to determine a median threshold based on RRI, the CA signals can also be utilized to determine an averaged, or median morphology of CA signal. This CA signal morphology can then be compared to the morphology of future CA signals to determine if a PVC is presented. Again, by utilizing the most recent CA signal morphology, factors such as posture, movement, exercise, etc. that may naturally affect the CA signal morphology is considered to prevent a false detection of a PVC. In this manner, the COIs obtained may be compared and analyzed against the most relevant CA signals.

At 316, after updating the CA signal morphology, a determination is made whether a previous beat had been a PVC. If the previous beat had been a PVC, then the one or more processor goes back to monitoring the CA signals. In an example embodiment when the COI is the RRI, if the previous beat was not a PVC, then at 318, the one or more processors update the RRI threshold. Specifically, the oldest CA signal recorded in the memory is discarded, and the RRI is included in the determination of the threshold for analyzing the next CA signal. After updating the RRI threshold, again, the one or more processors continue monitoring CA signals.

If at 312, a determination is made that the CA signal for the series of beats includes a PVC, at 320 the one or more processors mark the beat as a PVC. In one example, the CA signal morphology of the current beat is compared to a median of recent beat that were not determined to include a PVC. If the CA signal morphology differs from the median by a threshold, then the CA signal of the beat is considered to include a PVC. In one embodiment, the COI of the CA signal and average COIs of previous CA signals are compared. In one example, the area underneath a CA signal is compared to the median area underneath the previous measured and recorded CA signals. If such comparison is different by more than a threshold percentage, such as 20%, a PVC is identified. In another example, the amplitudes of the CA signal are compared to a median amplitude of the previous measured and recorded CA signals. In another example, frequency, intervals, shape, or the like is compared. The comparison may be made utilizing a mathematical model, mathematical equation, lookup table, etc. In example embodiments, more than one COI is considered when making the identification. In this manner, with more variables considered, more accuracy is similarly presented.

At 322, the one or more processors determine if a determined number of the series of beats in a row are considered a PVC. In particular, if a patient has a changed posture, is exercising, etc., or if a faulty reading is causing the median to be incorrect, etc. this may be an indication that PVCs are not presented. So, if the determined number is not reached, the one or more processors continue to monitor the CA signals. However, if the determine number is reached, then at 324 then both the RRI and morphology are updated with the PVC identified RRIs and morphology. Specifically, while typically the CA signal with the identified PVC is not utilized in the RRI threshold and morphology threshold determination, after the number is reached, then each CA signal is utilized for RRI threshold and morphology threshold determinations. So, in one example, four straight beats are considered the determined number. So, if three straight identified beats are presented, none of those CA signals is utilized to determine the RRI threshold or the morphology threshold. However, upon identification of the fourth straight beat, the oldest four RRI and morphology determinations are discarded, and all four of the CA signals with the identified PVCs are utilized to determine the RRI threshold and morphology threshold. In another example, upon identification of the fifth straight PVC beat, the CA signal of the fifth beat is added to the RRI and morphology rolling buffers in first-in first-out fashion.

The PVC detection algorithm is designed to ensure high specificity at the expense of reduced sensitivity. The sensitivity and specificity of the algorithm were evaluated on a training dataset consists of 94 ICM recordings with a total duration of 832 minutes and a testing dataset consists of 100 ICM recordings with a total duration of 864 minutes. Each ICM recording was manually adjudicated for PVCs, oversensing, and R-wave undersensing. In the training dataset, the algorithm demonstrates a sensitivity of 78.6%, specificity of 99.5%, PPV of 70.8%, and NPV of 99.7%. In the testing dataset, the algorithm achieved a sensitivity of 75.8%, specificity of 99.7%, PPV of 82.7%, and NPV of 99.5%.

Figure 5A:
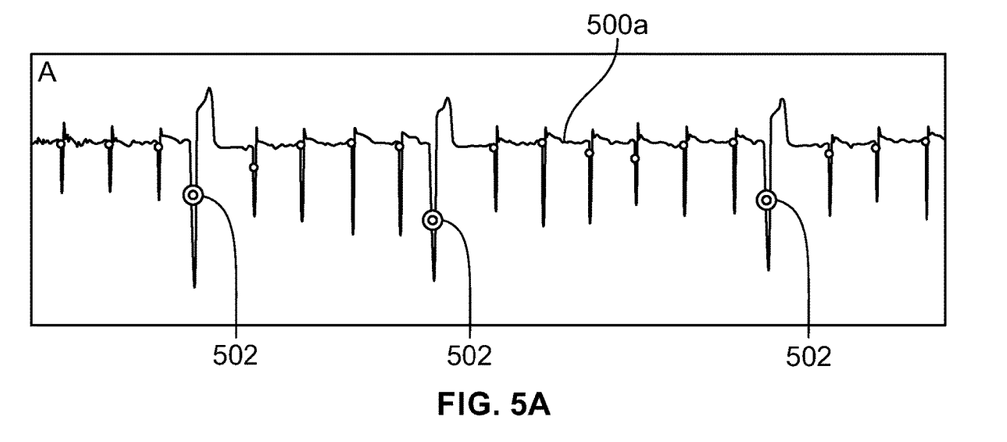
FIG. 5A illustrates of graph of a CA signal in accordance with embodiments herein.
Figure 5B:
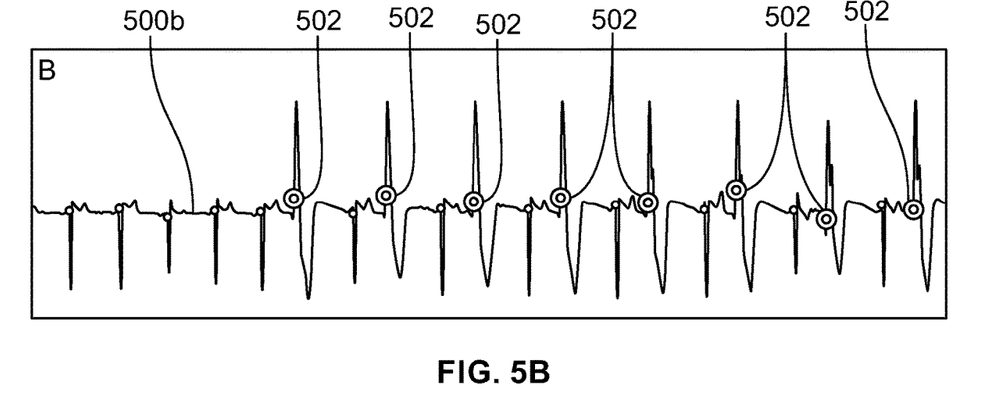
FIG. 5B illustrates of graph of a CA signal in accordance with embodiments herein.
Figure 5C:
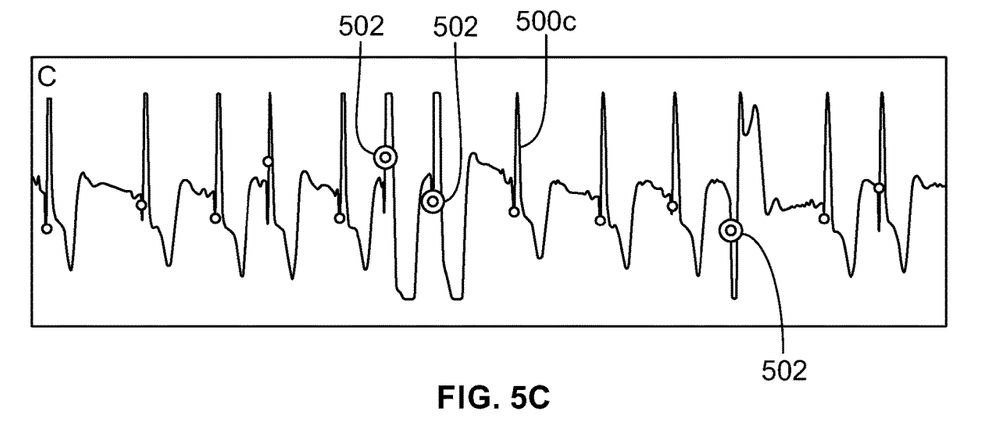
FIG. 5C illustrates of graph of a CA signal in accordance with embodiments herein.

With attention drawn to FIGS. 5A, 5B, and 5C, example detected CA signals 500A, 500B, and 500C that include PVCs 502 are provided. Utilizing the method of FIG. 3, not only can a PVC 502 be identified, but in addition, the type of PVC may also be identified. For example, FIG. 5A illustrates an isolated PVC 502, whereas FIG. 5B illustrates a train of bigeminy PVCs 502, and FIG. 5C illustrates double PVCs 502 with an isolated PVC 502.

In particular, because the PVC identification method identifies PVCs on a beat-by-beat basis, the method is capable of identifying different types of PVCs. Example types of PVCs include ventricular bigeminy, trigeminy, couplets (e.g. two consecutive PVC beats), triplets (three consecutive PVC beats), non-sustained or isolated PVCs, etc. As a result, a clinician has more information for diagnosis and analysis purposes, improving functionality.

Figure 6:
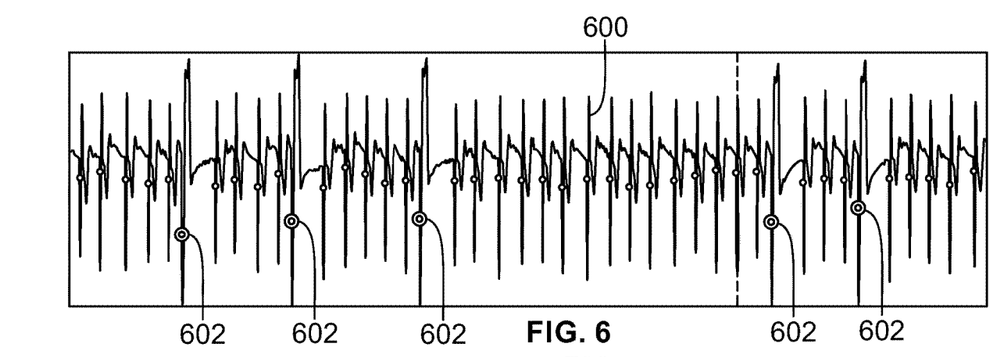
FIG. 6 illustrates of graph of a CA signal in accordance with embodiments herein.

For example, The PVC identification method can be utilized as a discriminator to improve AF detection specificity by reducing false AF detection due to frequent PVCs. FIG. 6 illustrates an example CA signal 600 where the PVCs 602 can cause the determination of a false AF detection. By knowing of the PVCs, including the types of PVCs such false AF detection can be avoided.

In one embodiment, when the number of PVCs during a determined period exceeds a threshold, any AFs detected by an ICM may be identified as a false AF detection. In one example, after the AF is determined, a verification process is undertaken where the number of PVCs within an AF period is counted. If the number of PVCs exceeds the threshold number, the AF identified may be discarded. Alternatively, the reading may identify the AF as false based on a PVC determination to provide information to a clinician to provide additional scrutiny to the discarded AF. To this end, the one or more processors can analyze the CA signal for an interval stability check, after eliminating the intervals associated with the PVC beats (e.g. each PVC has two associated intervals, the premature interval, and the post-PVC interval). The AF detection can then be rejected if the remaining intervals are stable.

In another embodiment, the number of PVCs in the determined period is a variable utilized to determine if an AF has occurred. So, instead of verification, the PVCs are a variable that is utilized to make the AF identification. Such determination may be made by a mathematical function, mathematical model, lookup table, decision tree, or the like.

In another example, the PVC identification may be utilized in an existing algorithm, model, etc. such as use in correcting R-wave amplitude. Specifically, co-pending U.S. application Ser. No. 16/589,978, filed Oct. 1, 2019 entitled Method and Systems for Reducing False Declarations of Arrythmias that is hereby incorporated by reference in its entirety herein provides such an R-wave amplitude correction based on posture. The PVC identification may also be utilized in addition to posture variances to correct the R-wave amplitude to again prevent false AFs from being diagnosed.

Figures 7A, 7B:
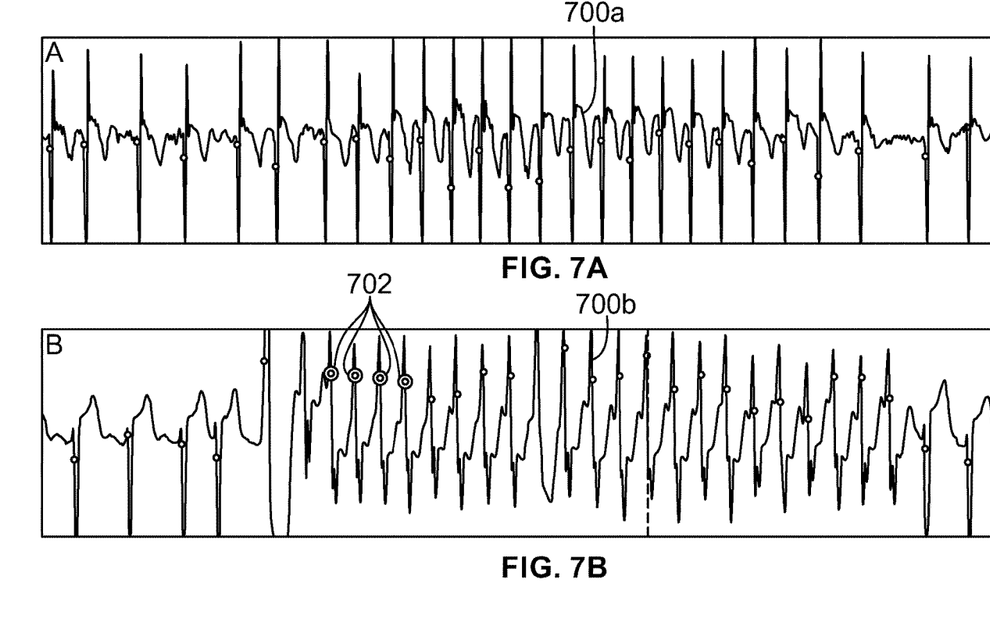
FIG. 7A illustrates of graph of a CA signal in accordance with embodiments herein.
FIG. 7B illustrates of graph of a CA signal in accordance with embodiments herein.

In another example of utilization of identification of the PVC and PVC types, the PVCs and PVC types can be utilized to discriminate supraventricular tachycardias (SVTs) from ventricular tachycardias (VTs). FIG. 7A illustrates a CA signal 700 of a tachycardia that can often be misdiagnosed as a VT instead of an SVT. The PVC identification method as described in FIG. 3 can specifically be used to identify the tachycardia episodes that are more likely to be VT rather than SVT. In particular, SVT beats have similar morphology to intrinsic beat, and as a result would not trigger PVC detection.

Alternatively, as illustrated in FIG. 7B that illustrates a CA signal 702 that is a VT, the detected PVCs 704 can be utilized to diagnose the VT. Specifically, if the percentage of PVC beats in the CA signal exceeds a threshold, or the consecutive PVC beats exceed a threshold, the tachycardia is more likely to be VT instead of SVT. In another example, the percentage of PVC beats that exceed the threshold, or the number of consecutive PVC beat that exceed a threshold are either identified to a clinician, or utilized in an analysis to determine if the tachycardia is VT or SVT. By identifying to a clinician, an EGM review burden for finding a VT can be reduced.

In yet another example embodiment, the PVC identification can be utilized as a bio monitor. As an indirect measure of autonomic dysfunction, heart rate variability (HRV) has been demonstrated to have a strong association with heart failure (HF) severity. Because HRV is calculated using RRIs between intrinsic beats, the PVC methodology allows a more accurate HRV evaluation by excluding the RRIs associated with PVC beats. Similarly, the PVC methodology also allows the ignoring of a period of time with frequent PVCs when determining the HF severity.

In addition, the PVC methodology also enables heart rate turbulence (HRT) monitoring by tracking the short-term fluctuation in sinus cycle length that follows a PVC. As a baroreflex-mediated biphasic reaction of HR in response to PVCs, HRT is demonstrated to predict mortality and sudden cardiac death following myocardial infarction. To monitor HRT, a set number of RRIs following a PVC are evaluated to determine if a biphasic reaction (e.g. a HR increase followed by a HR reduction) occurred.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system, comprising:
   a sensing circuit configured to detect CA signals for a series of beats;
   one or more processors; and
   a memory coupled to the one or more processors, wherein the memory stores program instructions, wherein the program instructions are executable by the one or more processors to:
   obtain, with a premature ventricular contraction (PVC) identification system via the sensing circuit, candidate cardiac activity (CA) signals for the series of beats;
   identify, with the PVC identification system, whether a characteristic of interest (COI) from a first segment of the candidate CA signals exceeds a COI limit;
   analyze, with the PVC identification system, morphology of the candidate CA signals for the series of beats responsive to the first segment of the candidate CA signals exceeding the COI limit; and
   based on the analyze operation, identify, with the PVC identification system, a PVC within the series of beats;
   discard the candidate CA signals if the PVC is identified within the candidate CA signals based on the analyze operation;
   add the candidate CA signals to the series of beats and discarding another beat of the series of beats if a PVC is not identified within the candidate CA signals based on the analyze operation; and
   repeat the obtain, identify, analyze, operations to identify an additional PVC in the series of beats.

2. The system of claim 1, wherein to identify whether the COI from the first segment of the CA signals exceeds the COI limit comprises:
   comparing a R-R interval (RRI) of a candidate beat to a RRI related to the series of beats; and
   determining whether a change in the RRI of the candidate beat compared to the RRI related to the series of beats exceeds a threshold.

3. The system of claim 2, wherein the RRI related to the series of beats is a mean RRI of the series of beats.

4. The system of claim 2, wherein the program instructions are executable by the one or more processors further to:
   analyze RRIs of additional candidate beats responsive to identifying the PVC of the candidate beat; and
   determine whether a biphasic reaction occurred in the series of beats.

5. The system of claim 1, wherein to analyze morphology of the CA signals for the series of beats comprises determining at least one of an area of the CA signals, a maximum amplitude of the CA signals, or a minimum amplitude of the CA signals.

6. The system of claim 1, wherein the program instructions are executable by the one or more processors further to:
   determine a type of PVC based on the PVC and the additional PVC.

7. The system of claim 1, wherein the program instructions are executable by the one or more processors further to:
   reject an atrial fibrillation (AF) diagnosis based on identification of the PVC.

8. The system of claim 1, wherein the program instructions are executable by the one or more processors further to:
   diagnose a type of tachycardia episode based on the identification of the PVC.

9. The system of claim 1, wherein the program instructions are executable by the one or more processors further to:
   discard the RRI of a candidate beat from a heart rate variability (HRV) diagnosis determination responsive to identifying the PVC of the candidate beat.

10. A computer implemented method for identifying a premature ventricular contraction (PVC), comprising:
    under control of one or more processors configured with specific executable instructions,
    obtaining, with a premature ventricular contraction (PVC) identification system via a sensing circuit, candidate cardiac activity (CA) signals for a series of beats;
    identifying, with the PVC identification system, whether a characteristic of interest (COI) from a first segment of the candidate CA signals exceeds a COI limit;
    analyzing, with the identification PVC system, morphology of the candidate CA signals for the series of beats responsive to the first segment of the CA signals exceeding the COI limit;
    based on the analyzing operation, identifying, with the PVC identification system, a PVC within the series of beats;
    discarding the candidate CA signals if the PVC is identified within the candidate CA signals based on the analyze operation;
    adding the candidate CA signals to the series of beats and discarding another beat of the series of beats if a PVC is not identified within the candidate CA signals based on the analyze operation; and
    repeating the obtaining, identifying, analyzing, operations to identify an additional PVC in the series of beats.

11. The method of claim 10, wherein identifying whether the COI from the first segment of the CA signals exceeds the COI limit comprises:
    comparing a R-R interval (RRI) of a candidate beat to a RRI related to the series of beats; and
    determining whether a change in the RRI of the candidate beat compared to the RRI related to the series of beats exceeds a threshold.

12. The method of claim 11, further comprising:
    analyzing RRIs of additional candidate beats responsive to identifying the PVC of the candidate beat; and
    determining whether a biphasic reaction occurred in the series of beats.

13. The method of claim 12, wherein the RRI related to the series of beats is a mean RRI of the series of beats.

14. The method of claim 10, wherein analyzing morphology of the CA signals for the series of beats comprises determining at least one of an area of the CA signals, a maximum amplitude of the CA signals, or a minimum amplitude of the CA signals.

15. The method of claim 10, further comprising:
determining a type of PVC based on the PVC and the additional PVC.

16. The method of claim 10, further comprising:
rejecting an atrial fibrillation (AF) diagnosis based on identification of the PVC.

17. The method of claim 10, further comprising:
diagnosing a type of tachycardia episode based on the identification of the PVC.

18. The method of claim 10, further comprising:
discarding the RRI of a candidate beat from a heart rate variability (HRV) diagnosis determination responsive to identifying the PVC of the candidate beat.

\* \* \* \* \*